United States Patent
Bonetti et al.

(10) Patent No.: US 9,884,829 B2
(45) Date of Patent: Feb. 6, 2018

(54) PROCESS FOR THE PREPARATION OF TETRACONAZOLE

(71) Applicant: ISAGRO S.P.A., Milan (IT)

(72) Inventors: Roberto Bonetti, Cologno Monzese (IT); Giampaolo Zanardi, Novara (IT)

(73) Assignee: ISAGRO S.P.A., Milan (IT)

( * ) Notice: Subject to any disclaimer, the term of this patent is extended or adjusted under 35 U.S.C. 154(b) by 0 days.

(21) Appl. No.: 15/533,988

(22) PCT Filed: Dec. 12, 2014

(86) PCT No.: PCT/IT2014/000331
§ 371 (c)(1),
(2) Date: Jun. 7, 2017

(87) PCT Pub. No.: WO2016/092573
PCT Pub. Date: Jun. 16, 2016

(65) Prior Publication Data
US 2017/0327473 A1    Nov. 16, 2017

(51) Int. Cl.
| | |
|---|---|
| *C07D 249/08* | (2006.01) |
| *C07C 17/278* | (2006.01) |
| *C07C 41/06* | (2006.01) |
| *C07C 41/38* | (2006.01) |
| *C07C 43/12* | (2006.01) |
| *C07C 25/08* | (2006.01) |
| *C07C 19/08* | (2006.01) |
| *A01N 43/653* | (2006.01) |

(52) U.S. Cl.
CPC ......... *C07D 249/08* (2013.01); *A01N 43/653* (2013.01); *C07C 17/278* (2013.01); *C07C 19/08* (2013.01); *C07C 25/08* (2013.01); *C07C 41/06* (2013.01); *C07C 41/38* (2013.01); *C07C 43/12* (2013.01); *C07B 2200/07* (2013.01)

(58) Field of Classification Search
None
See application file for complete search history.

(56) References Cited

FOREIGN PATENT DOCUMENTS

| | | |
|---|---|---|
| CN | 101020664 A | 8/2007 |
| EP | 0234242 A2 | 9/1987 |
| IT | 1375270 | 6/2010 |

OTHER PUBLICATIONS

Italian Patent Office notice of patent grant of IT MI2006A002386 as IT1375270 dated Jun. 7, 2010.
Espacenet Bibliographic Data for IT MI2006A002386 A1 dated Jun. 14, 2008 which corresponds to IT 1375270 granted Jun. 7, 2010.
Bianchi, Daniele, et al., Chemoenzymic Synthesis and Biological Activity of Both Enantiomeric Forms of Tetraconazole, A New Antifungal Triazole, Journal of Agricultural and Food Chemistry, Jan. 1, 1991, pp. 197-201, vol. 39.
Bianchi, Daniele, et al., Enzymatic Preparation of Optically Active Fungicide Intermediates in Aqueous and in Organic Media, Pure and Applied Chemistry, Jan. 1, 1992, pp. 1073-1078, vol. 64—No. 8.
Notification of Transmittal of the International Search Report and the Written Opinion of the International Searching Authority for PCT/IT2014/000331 dated May 27, 2015.

*Primary Examiner* — Alicia L Otton
(74) *Attorney, Agent, or Firm* — Hedman & Costigan, P.C.; James V. Costigan; Kathleen A. Costigan

(57) ABSTRACT

The present invention relates to a new process for the preparation of Tetraconazole or one of its optically active isomers by means of the fluorination of 2-(2,4-dichlorophenyl)-3-(1H-1,2,4-triazol-1-yl)propan-1-ol.

19 Claims, No Drawings

PROCESS FOR THE PREPARATION OF TETRACONAZOLE

The present invention relates to a new process for the preparation of Tetraconazole or one of its optically active isomers by means of the fluorination of 2-(2,4-dichlorophenyl)-3-(1H-1,2,4-triazol-1-yl)propan-1-ol.

DESCRIPTION

Tetraconazole, i.e. 2-(2,4-dichlorophenyl)-3-(1H-1,2,4-triazol-1-yl)propyl-1,1,2,2-tetrafluoroethylether having the following chemical structure:

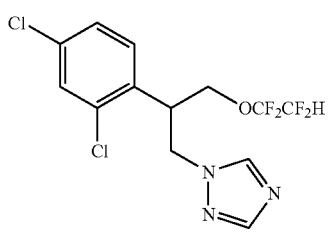

(I)

is a triazole fungicide with a broad spectrum, whose action is exerted by inhibiting the biosynthesis of ergosterol, a component that plays an important role in the formation, stability and functioning of fungal cell membranes.

Tetraconazole is traditionally used in its racemic form, but can also be used as an optically active isomer, i.e. as (R) or (S) isomer.

Few processes are described in literature for the preparation of Tetraconazole, either in racemic or optically active form.

EP234242 describes the preparation of Tetraconazole by means of the fluorination of the corresponding alcohol, 2-(2,4-dichlorophenyl)-3-(1H-1,2,4-triazol-1-yl)propanol with tetrafluoroethylene, in anhydrous dimethylformamide in the presence of sodium iodide (added in the form of an oily suspension).

Bianchi D. et al. J. Agric. Food Chem 1991, 39, 197-201 describe the synthesis of the (R) isomer and (S) isomer of Tetraconazole by means of the fluorination of the corresponding optically active alcohols with tetrafluoroethylene, in the presence of finely ground potassium hydroxide in a mixture of dimethylsulfoxide and toluene.

The above processes lead to the formation of various impurities, among which 1-[2-(2,4-dichlorophenyl)propen-2-yl]-1H-1,2,4-triazole in a quantity equal to about 5% by weight, therefore making it necessary to purify the product by means of chromatography.

The necessity is therefore felt for finding a new easily industrializable process that allows Tetraconazole or one of its optically active isomers to be obtained with a greater selectivity (higher purity), thus possibly avoiding resort to subsequent purification phases.

The Applicant has now surprisingly found that the addition of a certain quantity of water to the reaction mixture subjected to fluorination allows Tetraconazole, or one of its optically active isomers, to be obtained with high yields and a higher selectivity with respect to what can be obtained with the processes of the known art.

The object of the present invention therefore relates to a process for the preparation of Tetraconazole or one of its optically active isomers having formula (I):

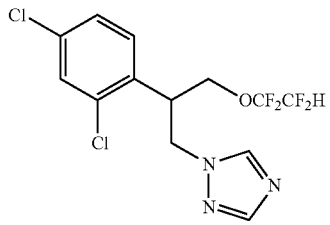

(I)

which comprises reacting the compound 2-(2,4-dichlorophenyl)-3-(1H-1,2,4-triazol-1-yl)propan-1-ol having formula (II), or one of its optically active isomers,

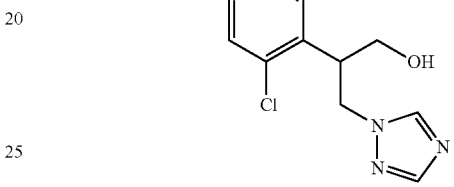

(II)

dissolved or suspended in at least one organic solvent, with tetrafluoroethylene in the presence of water and an inorganic base to form said Tetraconazole having formula (I) or one of its optically active isomers.

A preferred embodiment of the process according to the present invention is described hereunder.

The compound having general formula (II) can be obtained by means of synthetic methods well-known to skilled persons in the field, such as those described, for example, in EP234242 or in IT1375270, incorporated herein by reference.

According to the present invention, the compound having general formula (II) is dissolved or suspended in at least one polar or apolar organic solvent, or in a mixture thereof. Preferred examples of polar solvents are: dimethylsulfoxide, dimethylformamide, N-methylpyrrolidone or mixtures thereof. Preferred examples of apolar solvents are: toluene, xylenes or mixtures thereof.

The fluorination reaction with tetrafluoroethylene of the compound having general formula (II) is preferably carried out in a mixture of solvents comprising at least one apolar organic solvent or one polar organic solvent.

The term "fluorination" according to the present invention refers to a nucleophilic addition of the compound having general formula (II) on tetrafluoroethylene.

Preferably, said compound having general formula (II) is dissolved in at least one polar solvent and at least one apolar solvent is added to the solution thus obtained.

According to a further preferred aspect, the compound having general formula (II) is suspended in a mixture of at least one polar solvent and at least one apolar solvent. Said at least one polar solvent is more preferably dimethylsulfoxide and said at least one apolar solvent is toluene.

The polar solvent (e.g. dimethylsulfoxide) and the apolar solvent (e.g. toluene) are present in the above mixture of solvents in a volume ratio preferably ranging from (1:1) to (1:20), more preferably from (1:2) to (1:10), even more preferably about (1:5).

According to a preferred embodiment of the process according to the present invention, the reaction mixture containing at least the compound having general formula (II) dissolved or suspended in at least one organic solvent, is brought to a temperature ranging from 0° C. to −20° C., more preferably to about −10° C.

A certain quantity of at least one inorganic base, such as a hydroxide of an alkaline metal, selected for example, from sodium hydroxide and potassium hydroxide, is added to the reaction mixture at the above temperature. Said hydroxide of an alkaline metal is preferably potassium hydroxide.

According to a preferred aspect of the present invention, the inorganic base is added to the reaction mixture in a weight quantity ranging from 1% to 10%, more preferably from 2% to 5%, with respect to the weight of the compound having general formula (II).

Said inorganic base can be used in solid form or as aqueous solution.

According to the present invention, the fluorination reaction takes place in the presence of a certain quantity of water in the reaction mixture. The water is added to the reaction mixture as further solvent in the dissolution or suspension phase of the compound having general formula (II) or as part of the aqueous solution of the above inorganic base added to the reaction mixture.

The quantity by weight of water added preferably ranges from 1% to 5%, more preferably from 2% to 4%, even more preferably is about 2.5% by weight with respect to the weight of the compound having general formula (II).

Once the reaction mixture has been introduced into the reactor, the reactor is fed with gaseous tetrafluoroethylene and the mixture is left to react, under stirring. The reaction is carried out for a period of time preferably ranging from one to five hours; the temperature preferably ranges from −10° C. to −5° C.; the pressure preferably ranges from 1 bar to 1.5 bar.

Possible impurities in the form of solid particles in suspension in the reaction mixture are subsequently filtered and separated from the liquid phase of said mixture.

The liquid phase is generally subjected to one or more extraction treatments with water in order to extract the polar solvent in an aqueous phase and separate it from the remaining organic phase containing Tetraconazole and possible by-products of the fluorination reaction. If desired, the polar solvent can be recovered from the aqueous phase, for example by distillation.

According to the present invention, the filtration phase for eliminating the solid impurities can be effected in one or more moments of the process, for example: (i) during the fluorination reaction, (ii) on the reaction mixture before the extraction phase with water, (iii) on the organic phase after extraction with water and separation of the aqueous phase or on the final product, after this has been recovered from the organic phase in liquid form.

The polar solvent recovered from the aqueous phase can be optionally recycled to the process according to the present invention.

The Tetraconazole can be recovered from the organic phase, after the polar solvents possibly present have been separated therefrom, using separation techniques known to skilled persons in the field.

The organic phase, for example, is concentrated under vacuum to directly provide high-purity Tetraconazole or one of its optically active isomers, i.e. with a purity preferably equal to or higher than 96%. In many applications, this degree of purity is sufficiently high and it is therefore not necessary to subject the product to further purification phases. If desired, however, the product can be further purified with techniques and devices known in the art.

Thanks to the use of water in the reaction mixture subjected to fluorination, the process of the present invention therefore allows Tetraconazole or one of its optically active isomers to be obtained with a higher selectivity with respect to the processes of the known art, and possibly recycling the polar solvents used in the process; this makes the process according to the present invention particularly advantageous with respect to its industrial applicability.

EXPERIMENTAL PART

Example 1: Preparation of Tetraconazole with Solid KOH 100.0 grams of 2-(2,4-dichlorophenyl-3-(1H-1,2,4-triazol-1-yl)propan-1-ol are suspended in a mixture of toluene (875 mL) and DMSO (180 mL) in a glass reactor having a volume of 2 liters, equipped with a cooling jacket and mechanical anchor stirrer.

The mass is cooled to a temperature of −10° C. and 4.4 grams of finely ground potassium hydroxide and 2.5 mL of water are added.

A vacuum is established in the reactor up to a residual pressure of about 25 mbar, which is released by feeding gaseous tetrafluoroethylene from a reserve, at a pressure of about 1.1 bar.

The reaction mixture is stirred for about 2 hours at a temperature ranging from −10° C. to −5° C., and is then filtered on a cellulose filter and extracted three times consecutively with aliquots of 200 mL of water, each time separating the organic phase from the aqueous phase.

The organic phase is completely evaporated to obtain a liquid residue of Tetraconazole having a weight of 135 grams and a purity higher than 96% by weight.

The product thus obtained contains from 1% to 1.5% by weight of the main impurity: 1[2-(2,4-dichlorophenyl)propen-2-yl]1H-1,2,4-triazole.

Example 2: Preparation of Tetraconazole with an Aqueous Solution of KOH 100.0 grams of 2-(2,4-dichlorophenyl-3-(1H-1,2,4-triazol-1-yl)propan-1-ol are suspended in a mixture of toluene (875 mL) and DMSO (180 mL) in a glass reactor having a volume of 2 liters, equipped with a cooling jacket and mechanical anchor stirrer.

The mass is cooled to a temperature of −10° C. and 5.0 grams of an aqueous solution at 50% by weight of potassium hydroxide are added.

A vacuum is established in the reactor up to a residual pressure of about 25 mbar, which is released by feeding gaseous tetrafluoroethylene from a reserve, at a pressure of about 1.1 bar.

The reaction mixture is stirred for about 4 hours at a temperature ranging from −10° C. to −5° C., and is then extracted three times consecutively with aliquots of 200 mL of water, each time separating the organic phase from the aqueous phase.

The organic phase is filtered on a cellulose filter. The organic phase is then completely evaporated to obtain a liquid residue of Tetraconazole having a weight of 133 grams and a purity higher than 96% by weight.

The product thus obtained contains from 1% to 1.5% y weight of the main impurity: 1[2-(2,4-dichlorophenyl)propen-2-yl]1H-1,2,4-triazole.

Example 3

100.0 grams of 2-(2,4-dichlorophenyl-3-(1H-1,2,4-triazol-1-yl)propan-1-ol are dissolved in 180 mL of DMSO at a temperature of 40° C. 4.4 grams of finely ground potassium hydroxide and 2.5 mL of water are then added. The solution obtained is combined with 875 mL of toluene in a glass reactor having a volume of 2 liters, equipped with a cooling jacket and mechanical anchor stirrer.

The mass is cooled to a temperature of −10° C. and a vacuum is established in the reactor up to a residual pressure of about 25 mbar, which is released by feeding gaseous tetrafluoroethylene from a reserve, at a pressure of about 1.1 bar.

The reaction mixture is stirred for about 4 hours at a temperature ranging from −10° C. to −5° C.

Optionally, instead of anchor stirring, the reactor can be equipped with a recirculation system by means of a pump which continuously removes the reaction mass from the bottom and re-introduces it from above by means of a nozzle, so that it penetrates the liquid and entrain the gas.

The organic phase is extracted three times consecutively with aliquots of 200 mL of water, each time separating the organic phase from the aqueous phase. The organic phase is stirred in the presence of solid sodium bicarbonate and then filtered. The organic phase is completely evaporated to obtain a liquid residue of Tetraconazole having a weight of 135 grams and a purity higher than 96%.

The product thus obtained contains from 1% to 1.5% by weight of the main impurity: 1[2-(2,4-dichlorophenyl)propen-2-yl]1H-1,2,4-triazole.

Example 4: (Comparative): Preparation of Tetraconazole According to the Procedure Described in Bianchi D. Et al. J. Agric. Food Chem 1991, 39, 197-201

100.0 grams of 2-(2,4-dichlorophenyl-3-(1H-1,2,4-triazol-1-yl)propan-1-ol are dissolved in a mixture of toluene (1250 mL) and DMSO (185 mL) in a glass reactor having a volume of 2 liters, equipped with a mechanical anchor stirrer.

The mass is cooled to a temperature of −5° C. and 11.5 grams of finely ground potassium hydroxide are added.

A vacuum is established in the reactor up to a residual pressure of about 25 mbar, which is released by feeding gaseous tetrafluoroethylene from a reserve, at a pressure of about 1.1 bar.

The reaction mixture is stirred for about 2 hours at a temperature of about −5° C., and is then extracted three times consecutively with cold water, each time separating the organic phase from the aqueous phase.

The organic phase is completely evaporated to obtain a liquid residue of Tetraconazole having a weight of 133 grams and a purity of 92% by weight.

The product thus obtained contains about 5% by weight of the main impurity: 1[2-(2,4-dichlorophenyl) propen-2-yl] 1H-1,2,4-triazole.

The invention claimed is:

1. A process for the preparation of Tetraconazole having formula (I), or one of its optically active isomers:

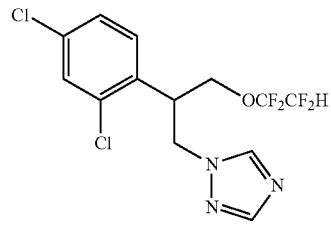

which comprises reacting the compound 2-(2,4-dichlorophenyl)-3-(1H-1,2,4-triazol-1-yl)propan-1-ol having formula (II), or one of its optically active isomers,

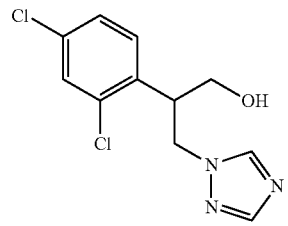

dissolved or suspended in at least one organic solvent, with tetrafluoroethylene in the presence of water and an inorganic base to form said Tetraconazole having formula (I) or one of its optically active isomers.

2. The process according to claim 1, wherein said water is present in a quantity within the range of 1%-10% by weight of said compound having formula (II).

3. The process according to claim 1, wherein said at least one organic solvent is a polar organic solvent selected from: dimethylsulfoxide, dimethylformamide, N-methylpyrrolidone or mixtures thereof.

4. The process according to claim 1, wherein said at least one organic solvent is an apolar organic solvent.

5. The process according to claim 1, wherein said reaction is carried out in a mixture of solvents which comprises at least one polar organic solvent and at least one apolar organic solvent.

6. The process according to claim 5, wherein the volume ratio between said polar organic solvent and said apolar organic solvent is within the range of 1:1 to 1:20.

7. The process according to claim 6, wherein said polar organic solvent is dimethylsulfoxide and said apolar organic solvent is toluene.

8. The process according to claim 5, wherein said polar organic solvent is dimethylsulfoxide and said apolar organic solvent is toluene.

9. The process according to claim 5, which comprises, after said reaction with tetrafluoroethylene, a phase for separating said polar solvent from said mixture of solvents.

10. The process according to claim 5, wherein the volume ratio between said polar organic solvent and said apolar organic solvent is within the range of 1:2 to 1:10.

11. The process according to claim 5, wherein the volume ratio between said polar organic solvent and said apolar organic solvent is about 1.5.

12. The process according to claim 1 wherein said inorganic base is selected from hydroxides of alkaline metals and mixtures thereof.

13. The process according to claim 12 wherein said inorganic base is selected from sodium hydroxide, potassium hydroxide and mixtures thereof.

14. The process according to claim 1, wherein said inorganic base is present in a quantity ranging from 1% to 10% by weight, with respect to the weight of said compound having general formula (II).

15. The process according to claim 14, wherein said inorganic base is present in a quantity ranging from 2% to 5% by weight, with respect to the weight of said compound having general formula (II).

16. The process according to claim 1, wherein said reaction with tetrafluoroethylene is carried out at a temperature ranging from −10° C. to −5° C.

17. The process according to claim 1, wherein said reaction with tetrafluoroethylene is carried out at a pressure ranging from 1 bar to 1.5 bar.

18. The process according to claim 1, wherein said polar solvent is separated from said mixture of solvents by extraction with water.

19. The process according to claim 1, wherein said water is present in a quantity within the range of 2%-4% by weight of said compound having formula (II).

* * * * *